US009508522B2

(12) United States Patent
Park et al.

(10) Patent No.: US 9,508,522 B2
(45) Date of Patent: Nov. 29, 2016

(54) X-RAY GENERATOR INCLUDING HEAT SINK BLOCK

(71) Applicants: Samsung Electronics Co., Ltd., Suwon-si (KR); SRI INTERNATIONAL, Menlo Park, CA (US)

(72) Inventors: Shang-hyeun Park, Yongin-si (KR); Paul R. Schwoebel, Menlo Park, CA (US); Il-hwan Kim, Yongin-si (KR); Do-yoon Kim, Yongin-si (KR); Yong-chul Kim, Yongin-si (KR); Chang-soo Lee, Yongin-si (KR); Tae-won Jeong, Yongin-si (KR)

(73) Assignees: SAMSUNG ELECTRONICS CO., LTD. (KR); SRI INTERNATIONAL, Menlo Park, CA (US)

( * ) Notice: Subject to any disclaimer, the term of this patent is extended or adjusted under 35 U.S.C. 154(b) by 182 days.

(21) Appl. No.: 14/207,216

(22) Filed: Mar. 12, 2014

(65) Prior Publication Data

US 2014/0270087 A1    Sep. 18, 2014

(30) Foreign Application Priority Data

Mar. 13, 2013 (KR) ........................ 10-2013-0026800

(51) Int. Cl.
*H01J 35/06* (2006.01)
*H01J 35/04* (2006.01)
(Continued)

(52) U.S. Cl.
CPC ............ *H01J 35/065* (2013.01); *A61B 6/4488* (2013.01); *H01J 1/304* (2013.01); *H01J 1/90* (2013.01);
(Continued)

(58) Field of Classification Search
CPC ....... B82Y 30/00; H01J 1/304; H01J 35/065; H01J 35/06; H01J 35/10; H01J 1/15; H01J 1/16; H01J 2235/06; H01J 2235/081; H01J 1/135; H01J 2201/2803; H01J 2201/281; H01J 2201/2867; H01J 2235/08; H01J 2235/087; H01J 2235/1204; H01J 2235/1212; H01J 1/00; H01J 1/02; H01J 1/30; H01J 1/88; H01J 1/90; H01J 1/94; H01J 1/96; H01J 2201/00; H01J 2201/30; H01J 2201/304; H01J 2201/30446; H01J 2201/30453; H01J 2201/30469; H01J 2201/3195; H01J 3/00; H01J 3/02; H01J 3/021; H01J 3/38; H01J 2203/00; H01J 2203/02; H01J 2203/0204; H01J 2203/0208; H01J 2203/0212; H01J 2203/0216; H01J 2203/0224; H01J 2203/0236; H01J 19/00; H01J 19/02; H01J 19/24; H01J 19/42; H01J 19/44; H01J 19/48; H01J 19/50; H01J 27/00; H01J 27/02; H01J 27/022; H01J 27/26; H01J 35/00; H01J 35/02; H01J 35/04; H01J 35/045; H01J 2235/062; H01J 2235/12; H01J 2235/1225; H01J 2235/1291; H01J 2235/1295; H01J 2237/03; H01J 2237/032; H01J 2237/036; H01J 2237/038; H01J 2237/06341; H01J 2237/06375; Y10S 977/742; Y10S 977/939; Y10S 977/95; H01M 10/6555; H01M 2/202; H01M 10/0481; H01M 10/613; H01M 2/0212; H01M 10/0413; H01M 10/4257; H01M 10/5055; H01M 10/625; H01M 10/647; H01M 10/6563; H01M 2010/4271; H01M 2220/20; H01M 2/1072; H01M 2/1077; A61B 6/00; A61B 6/40; A61B 6/4064; A61B 6/4488

USPC ........ 378/136, 142, 119, 141; 977/742, 939, 977/950

See application file for complete search history.

(56) References Cited

U.S. PATENT DOCUMENTS 5,726,524 A * 3/1998 Debe ..................... H01J 1/3042
204/192.1

(Continued)

FOREIGN PATENT DOCUMENTS

WO    WO 9742644 A1 * 11/1997 ............ H01J 1/3042

*Primary Examiner* — Anastasia Midkiff
(74) *Attorney, Agent, or Firm* — Cantor Colburn LLP

(57) ABSTRACT

An x-ray generator includes a housing, a cathode block that is arranged in the housing and emits electrons via a field emission scheme, an anode block that is arranged in the housing and generates x-rays in response to the electrons emitted from the cathode block and collide with the anode block, and a heat sink block that contacts the cathode block and dissipates heat generated therein to an outside of the housing.

16 Claims, 7 Drawing Sheets

(51) Int. Cl.
*H01J 19/44* (2006.01)
*H01J 3/02* (2006.01)
*H01J 3/38* (2006.01)
*H01J 1/30* (2006.01)
*H01J 1/90* (2006.01)
*A61B 6/00* (2006.01)
*H01J 1/304* (2006.01)
*H01J 19/24* (2006.01)
*H01J 19/42* (2006.01)
*B82Y 30/00* (2011.01)

(52) U.S. Cl.
CPC ............ *H01J 19/44* (2013.01); *H01J 35/045* (2013.01); *H01J 35/06* (2013.01); *A61B 6/40* (2013.01); *A61B 6/4064* (2013.01); *B82Y 30/00* (2013.01); *H01J 3/021* (2013.01); *H01J 3/38* (2013.01); *H01J 19/24* (2013.01); *H01J 19/42* (2013.01); *H01J 2201/304* (2013.01); *H01J 2201/30469* (2013.01); *H01J 2201/3195* (2013.01); *H01J 2203/0204* (2013.01); *H01J 2203/0208* (2013.01); *H01J 2203/0212* (2013.01); *H01J 2203/0216* (2013.01); *H01J 2203/0236* (2013.01); *H01J 2235/06* (2013.01); *H01J 2235/1212* (2013.01); *H01J 2235/1291* (2013.01); *H01J 2235/1295* (2013.01); *Y10S 977/742* (2013.01); *Y10S 977/939* (2013.01); *Y10S 977/95* (2013.01)

(56) References Cited

U.S. PATENT DOCUMENTS

| | | | | |
|---|---|---|---|---|
| 5,773,834 A * | 6/1998 | Yamamoto | ............ | B82Y 10/00 204/192.11 |
| 5,773,921 A * | 6/1998 | Keesmann | ............ | H01J 1/3042 313/309 |
| 5,973,444 A * | 10/1999 | Xu | ............ | H01J 1/304 313/309 |
| 6,019,656 A * | 2/2000 | Park | ............ | B82Y 10/00 445/24 |
| 6,259,765 B1 * | 7/2001 | Baptist | ............ | H01J 35/14 313/309 |
| 6,333,968 B1 * | 12/2001 | Whitlock | ............ | B82Y 10/00 378/122 |
| 6,385,292 B1 * | 5/2002 | Dunham | ............ | A61B 6/032 378/122 |
| 6,440,761 B1 * | 8/2002 | Choi | ............ | B82Y 10/00 313/309 |
| 6,485,345 B1 * | 11/2002 | Fushimi | ............ | H01J 9/027 445/24 |
| 7,085,351 B2 * | 8/2006 | Lu | ............ | A61B 6/4021 315/169.3 |
| 7,236,568 B2 * | 6/2007 | Dinsmore | ............ | H01J 35/065 378/119 |
| 7,522,706 B2 | 4/2009 | Lu et al. | | |
| 7,539,286 B1 * | 5/2009 | Bandy | ............ | H01J 1/135 378/121 |
| 7,839,980 B2 | 11/2010 | Lu et al. | | |
| 2002/0063500 A1 | 5/2002 | Keren | | |
| 2007/0057364 A1 * | 3/2007 | Wang | ............ | C03C 8/02 257/701 |
| 2009/0146158 A1 * | 6/2009 | Park | ............ | G02B 5/1876 257/89 |
| 2009/0245468 A1 * | 10/2009 | Zou | ............ | H01J 35/065 378/122 |
| 2009/0323898 A1 * | 12/2009 | Moore | ............ | H01J 1/15 378/136 |
| 2011/0249796 A1 * | 10/2011 | Okunuki | ............ | A61B 6/032 378/62 |
| 2012/0002789 A1 | 1/2012 | Lemarchand et al. | | |
| 2012/0207279 A1 | 8/2012 | Shimono | | |
| 2012/0250827 A1 * | 10/2012 | Jeong | ............ | H01J 35/14 378/122 |
| 2013/0214244 A1 * | 8/2013 | Sanborn | ............ | H01J 1/304 257/10 |

* cited by examiner

X-RAY GENERATOR INCLUDING HEAT SINK BLOCK

CROSS-REFERENCE TO RELATED APPLICATIONS

This application claims priority to Korean Patent Application No. 10-2013-0026800, filed on Mar. 13, 2013, and all the benefits accruing therefrom under 35 U.S.C. §119, the content of which in its entirety is herein incorporated by reference.

BACKGROUND

1. Field

The disclosure relates to a field-emission type x-ray generator including a heat sink.

2. Description of the Related Art

X-rays are used in various fields in the industry, science, and medicine for non-destructive inspections, structural and physical property inspections of materials, image diagnosis and security inspections, for example. Generally, a photographing device using x-rays includes an x-ray generator that emits x-rays, and a detector that detects x-rays that passed through an object.

The x-ray generator generally emits x-rays by making electrons emitted from a cathode collide with an anode. An electron-emitting device used in the x-ray generator may be divided into a cold cathode and a hot cathode. The electron-emitting device uses field emission and may be easily operated even with a low voltage. As such, many studies for developing electron-emitting devices that utilize field emission have been conducted.

In particular, a carbon nanotube may be used as an emitter in an electron-emitting device. Such an electron-emitting device where the carbon nanotube is used as an emitter therein may focus electrons via a high emitting current and have a relatively simple structure.

SUMMARY

In an X-ray generator, a high current is emitted by a high electric field, and the high current and the high electric field may negatively effect the structural stability between a cathode electrode and a gate electrode of the electron-emitting device.

Provided are embodiments of an electron-emitting device that generates a uniform electric field, and an x-ray generator including the electron-emitting device.

Provided are embodiments of an x-ray generator, in which heat generated by an electric current is effectively emitted.

Additional aspects will be set forth in part in the description which follows and, in part, will be apparent from the description, or may be learned by practice of the embodiments described herein.

According to an embodiment of the invention, an x-ray generator includes: a housing; a cathode block which is arranged in the housing and emits electrons via a field emission scheme; an anode block which is arranged in the housing and generates x-rays in response to the electrons that are emitted from the cathode block and collide with the anode block; and a heat sink which contacts the cathode block and disperses heat generated therein to an outside of the housing.

In an embodiment, a portion of the heat sink may be exposed to the outside of the housing.

In an embodiment, a concave-convex portion may be defined on the exposed portion of the heat sink.

In an embodiment, the heat sink may have a pillar shape, where one side of the pillar shape contacts the cathode block, and other side of the pillar shapes is exposed to the outside of the housing.

In an embodiment, the heat sink may have a shell shape with an empty space defined therein.

In an embodiment, the heat sink may have a circular cross-section, an oval cross-section, or a polygonal cross-section.

In an embodiment, the heat sink may include at least one of Cu, Al, Cr, Invar, ITO, Mo and W.

In an embodiment, an inside of the housing may be in a vacuum state.

In an embodiment, the cathode block may include: a cathode electrode; a plurality of emitters arranged on the cathode electrode; a mesh-type gate electrode arranged spaced apart from the cathode electrode; and an insulating layer arranged between the cathode electrode and the mesh-type gate electrode.

In an embodiment, a number of the emitters may be substantially inversely proportional to a volume of the heat sink.

In an embodiment, the cathode block may further include: a bonding layer arranged between the insulating layer and the mesh-type gate electrode.

In an embodiment, the bonding layer may include glass.

In an embodiment, the bonding layer may include glass frit.

In an embodiment, each of the emitters may include carbon nanotubes.

In an embodiment, a plurality of openings may be defined in the mesh-type gate electrode, and at least a portion of each of the emitters may be exposed by the openings.

In an embodiment, the insulating layer may include a plurality of gate spacers, and the emitters may be alternately arranged with the gate spacers.

In an embodiment, at least one of the insulating layer and the emitters may have a line shape.

In an embodiment, the x-ray generator may further include: a charge prevention film arranged on the insulating layer, where the charge prevention film may prevent the insulating layer from being electrically charged by electrons generated by the emitters.

In an embodiment, the insulating layer may include a plurality of gate spacers, and the charge prevention film may be arranged at a side surface of the gate spacers and may be connected to the mesh-type gate electrode.

In an embodiment, a resistivity of the charge prevention film may be between a resistivity of the mesh-type gate electrode and a resistivity of the gate spacers.

BRIEF DESCRIPTION OF THE DRAWINGS

These and/or other features of the invention will become more apparent by describing in further detail embodiments thereof with reference to the accompanying drawings, in which.

DETAILED DESCRIPTION

Figure 1:
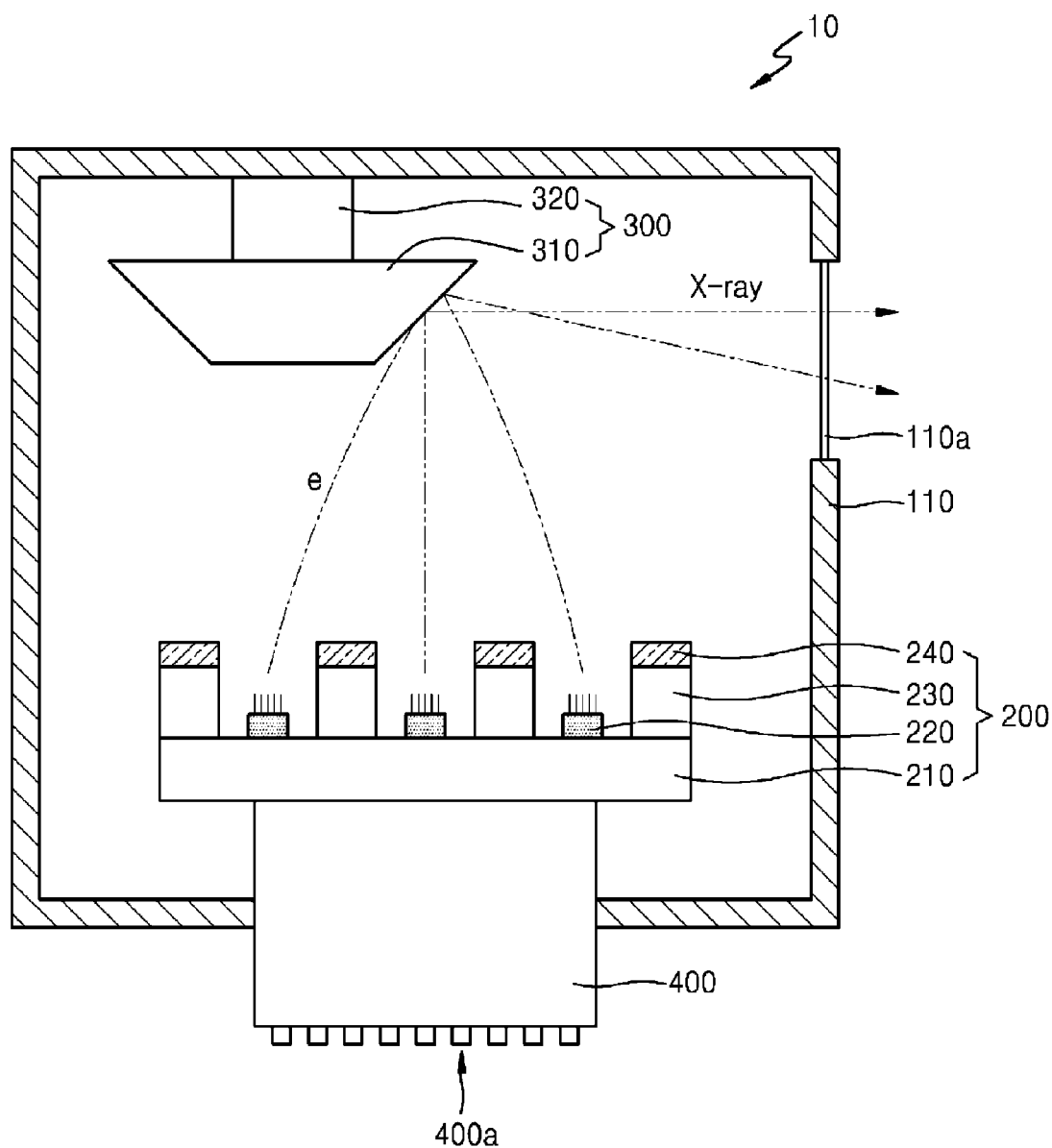
FIG. 1 is a view showing an embodiment of an x-ray generator, according to the invention.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within±30%, 20%, 10%, 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Embodiments of the invention are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

FIG. 1 is a view showing an embodiment of an x-ray generator 10, according to the invention.

Referring to FIG. 1, the x-ray generator 10 includes a housing 110, a cathode block 200 that is arranged within the housing 110 and emits electrons via a field emission scheme, and an anode block 300 that is arranged within the housing and generates x-rays in response to a collision thereof with electrons emitted from the cathode block 200. In such an embodiment, the x-ray generator 10 may further include a heat sink 400 that contacts the cathode block and disperses heat generated in the cathode block 200 to an outside of the housing 110.

The housing may have any shape, and may be in a sealed state such that the inside thereof is maintained substantially in a vacuum state. In an embodiment, one side of the housing 110 may include a window 110a for emitting x-rays to the outside of the housing 110. In such an embodiment, the housing 110 may further include an exhaust unit (not shown) connected to an external vacuum pump such that an internal gas in the housing 110 may be externally discharged. The housing 110 may include a material that may block x-rays, such as stainless, or glass, for example. In an embodiment, where the housing 110 includes glass, the housing 110 may further include an x-ray shield material for blocking the x-rays.

In such an embodiment, the window 110a may include a material that allows the x-rays to pass therethrough such that the x-rays may be externally emitted from the housing 110 while maintaining the internal vacuum state of the housing 110. In one embodiment, for example, the window 110a may include PYREX® glass or aluminum, for example.

In such an embodiment of the x-ray generator 10, when a voltage is applied to the cathode block 200, the cathode block 200 emits electrons via a field emission scheme. The cathode block 200 may include a cathode electrode 210, an emitter 220 that is arranged on the cathode electrode 210 and emits electrons, a gate spacer 230 that is arranged around the cathode electrode 210, and a gate electrode 240 that is arranged on the gate spacer 230. The cathode block 200 will be described later in greater detail.

In such an embodiment, the anode block 300 generates x-rays when electrons generated by the cathode block 200 collide thereon, and includes an anode electrode 310 including a metal such as Mo, Ag, W, Cr, Fe, Co and Cu, or a metal alloy thereof. In an embodiment, the anode block 300 may further include a driving unit 320 that drives the anode electrode 310 to control an area where electrons collide. In such an embodiment, when the electrons collide only on a certain area of the anode electrode 310, the certain area of the anode electrode 310 may be exaggeratedly heated, and thus, the lifespan of the x-ray generator 10 may be reduced. Accordingly, in such an embodiment, the driving unit 320 drives the anode electrode 310 to allow the electrons to be substantially evenly incident on the anode electrode 310. In one embodiment, for example, when the anode electrode 310 has a round plate shape, the driving unit 320 may rotate the anode electrode 310.

In an embodiment, the x-ray generator 10 may further include a heat sink 400 that externally disperses heat generated by the cathode block 200. The heat sink 400 may contact the cathode block 200 and a portion of the heat sink 400 may be exposed to the outside of the housing 110. In one embodiment, for example, the heat sink may have a pillar shape, one side of which may contact the cathode block 200 and other side of which may be externally exposed. In an alternative embodiment, the heat sink 400 may have a circular, oval or polygonal cross-section, for example, but not being limited thereto.

The heat sink 400 externally disperses heat generated by the cathode block 200, and the externally exposed area may have a shape that expands a surface of the exposed portion of the heat sink 400. In one embodiment, for example, a concave-convex portion 400a may be defined on a surface of the externally exposed portion of the heat sink 400. In an embodiment, the heat sink 400 may have a shell shape with an empty interior, and thus, a heat sink area thereof may be extended.

The heat sink 400 may include a metal having a substantially high thermal conductivity, such as Cr, Invar, Mo, W, Al and Cu, for example, and may further include a resin having a substantially high thermal conductivity. In an embodiment, the heat sink 400 may further include a heat sink paint applied on metal or resin materials. In such an embodiment, the heat sink paints may include indium tin oxide ("ITO"), tin oxide ($SnO_2$), zinc oxide (ZnO), indium zinc oxide ("IZO"), carbon nanotube, graphene or a combination thereof. In an embodiment, the heat sink 400 may include a black-type paint, such that heat may be effectively conducted and a heat sink effect may be obtained without separate equipment, thereby reducing manufacturing cost thereof.

Figure 2:
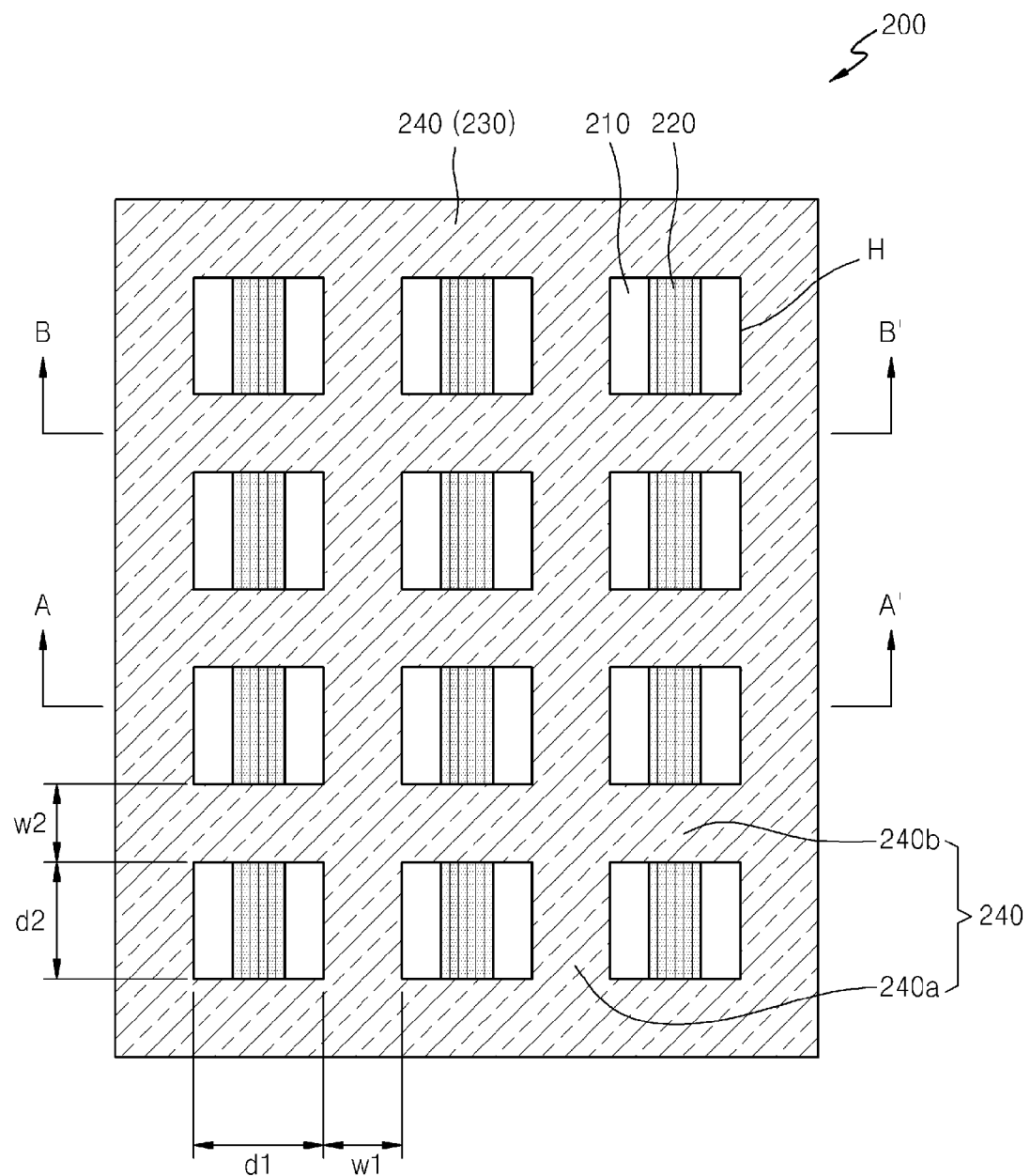
FIG. 2 is a plan view showing an embodiment of a cathode block of FIG. 1.
Figure 3A:
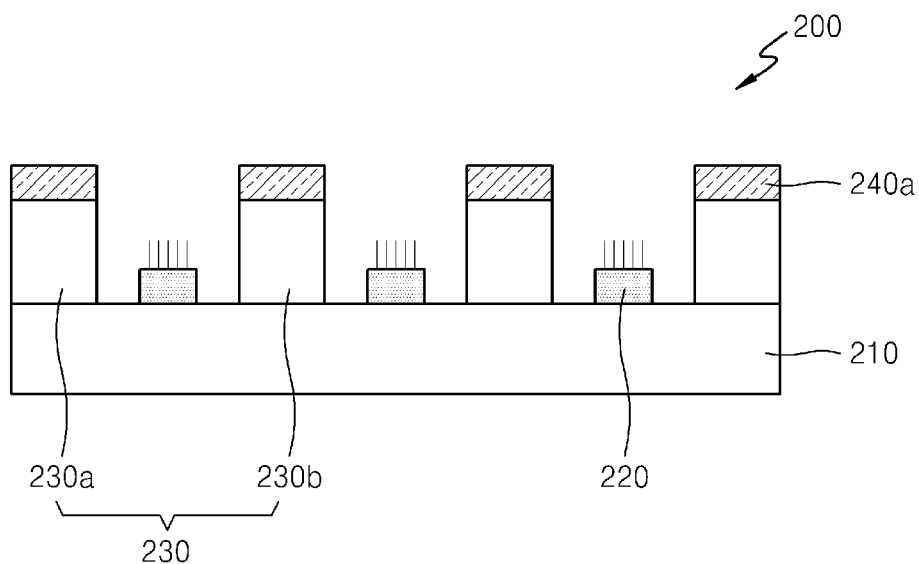
FIG. 3A is a cross-sectional view taken along line A-A' of the cathode block of FIG. 2.
Figure 3B:
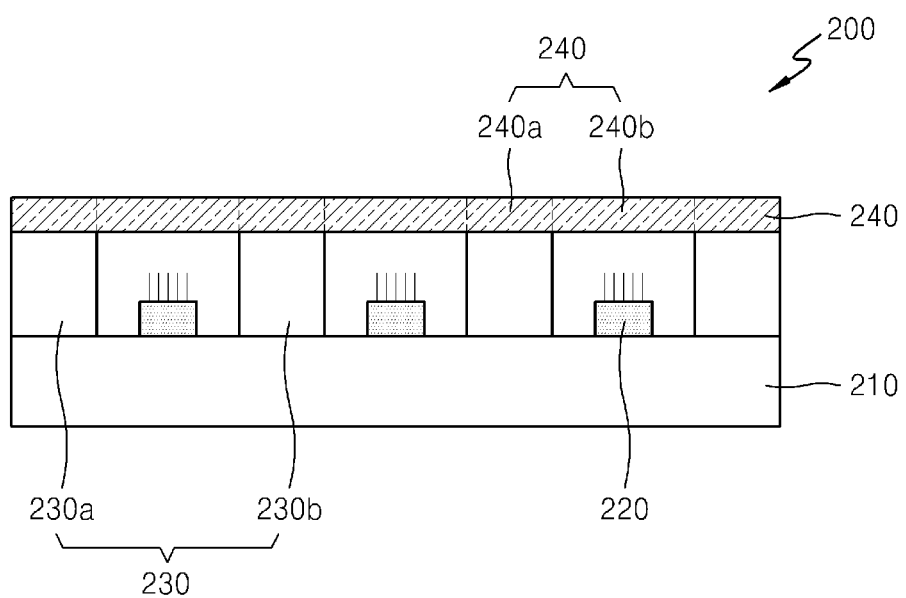
FIG. 3B is a cross-sectional view taken along line B-B' of the cathode block of FIG. 2.

FIG. 2 is a plan view showing an embodiment of the cathode block 200 of FIG. 1, FIG. 3A is a cross-sectional view taken along line A-A' of the cathode block 200 of FIG. 2, and FIG. 3B is a cross-sectional view taken along line B-B' of the cathode block 200 of FIG. 2.

Referring to FIGS. 2, 3A and 3B, the cathode block 200 may include a cathode electrode 210, a mesh-type gate electrode 240 that is disposed separately from the cathode electrode 210, a plurality of gate spacers 230 that extends substantially in a first direction between the cathode electrode 210 and the gate electrode 240, and a plurality of emitters 220.

Each of the cathode electrode 210 and the gate electrode 240 may include a conductive material such as a metal or a conductive metal oxide. In one embodiment, for example, the cathode electrode 210 and the gate electrode 240 may include a metal such as Ti, Pt, Ru, Au, Ag, Mo, Al, W or Cu or a metal oxide such as ITO, aluminum zinc oxide ("AZO"), IZO, $SnO_2$ or $In_2O_3$.

The cathode electrode 210 applies a voltage to the emitter 220, and may have a plane shape. In one embodiment, for example, the cathode electrode 210 may apply a ground voltage to the emitter 220. In such an embodiment, a voltage substantially equal to or different from the voltage applied to the cathode electrode 210 may be applied to the gate electrode 240, and the gate electrode 240 may induce the emitter 220 for emitting electrons. Accordingly, an embodiment of the x-ray generator 10, according to the invention, may have a triode structure including the cathode electrode 210, the gate electrode 240 and the anode electrode 310.

The gate electrode 240 may have a mesh structured including a plurality of openings H defined therein. In one embodiment, for example, the gate electrode 240 may include a plurality of gate lines 240a that are separately arranged on the gate spacer 230, and a plurality of gate bridges 240b that connect the plurality gate lines 240a. As such, an opening H is defined by two adjacent gate lines 240a and two adjacent gate bridges 240b. Each opening H may be arranged to correspond to the emitter 220 such that at least a portion of the emitter 220 between the gate spacers 230 is exposed.

In an embodiment, a width w1 of the gate line 240a may be substantially equal to or different from a width w2 of the gate bridge 240b. In such an embodiment, an interval d1 between gate lines 240a may be substantially equal to or different from an interval d2 between the gate bridges 240b. In one embodiment, for example, the interval d2 between the gate bridges 240b may be greater than the width of the gate bridge 240b, and the width d2 between the gate bridges 240b may be less than twice a distance between the emitter 220 and the gate electrode 240. If the interval d2 between the gate bridges 240b exceeds twice the distance between the emitter 220 and the gate electrode 240, the electric field formed on the emitter 220 may be substantially non-uniform. That is, when the interval d2 between the gate bridges 240b exceeds twice the distance between the emitter 220 and the gate electrode 240, a greater electric field is formed under the gate bridge 240b, and thus, electron emission of the emitter 220 becomes substantially uneven.

In such an embodiment, where the gate electrode 240 has a mesh structure, a large size cathode block 200 may be disposed. In one embodiment, as shown in FIG. 2, the opening H of the gate electrode 240 has a quadrilateral shape, but not being limited thereto. In an alternative embodiment, each of the openings H may have a circular, oval or polygonal shape. In such an embodiment, the sizes of the openings H may be substantially the same as each other or different from each other.

The gate spacer 230 may be arranged between the cathode electrode 210 and the gate electrode 240 to effectively prevent an electric current from flowing between the cathode electrode 210 and the gate electrode 240. In an embodiment, a plurality of gate spacers 230 may be arranged between the cathode electrode 210 and the gate electrode 240. In an embodiment, the gate spacer 230 may have linear shape. As such, the gate spacers 230 extend in a same direction, and are spaced apart from each other with a predetermined distance to support the gate electrode 240. The plurality of gate spacers 230 may include a first gate spacer 230a that supports an edge portion of the gate electrode 240 and a second gate spacer 230b that supports a central portion of the gate electrode 240.

The gate spacer 230 may include an insulating material, e.g., an insulating material typically used in a semiconductor device. In one embodiment, for example, the gate spacer 230 may include $SiO_2$, a high-K material having a permittivity higher than the permittivity of $SiO_2$, such as $HfO_2$, $Al_2O_3$ or $Si_3N_4$, or a combination of $HfO_2$, $Al_2O_3$ and $Si_3N_4$.

In an embodiment, the gate spacer 230 may be a line-shaped gate spacer 230 as illustrated in FIGS. 2 to 3B, but the invention is not limited thereto. In an alternative embodiment, the gate spacer 230 may have a different shape or structure that effectively prevents an electric current from flowing between the cathode electrode 210 and the gate electrode 240 and supports the gate electrode 240. In one embodiment, for example, the second gate spacer 230b may have a pillar shape and may be arranged on the lower side of the gate line 240a.

The emitter 220 emits electrons in response to a voltage applied to the cathode electrode 210 and the gate electrode 240. The cathode block 200 may include a plurality of emitters 220, and the plurality of emitters 220 may be arranged alternately with the plurality of gate spacers 230. In one embodiment, for example, the plurality of emitters 220 may be spaced apart from each other, and the second gate spacer 230b may be arranged between the plurality of emitters 220. In an embodiment, the emitter 220 may have a linear shape extending in the first direction as in the second gate spacer 230b. The gate electrode 240 has a mesh structure, and thus, the gate electrode 240 is arranged on the upper side of the emitter 220. As such, the emitter 220 may be disposed apart from the gate electrode 240 such that an electric short that may occur between the gate electrode 240 and the emitter 220 is effectively prevented.

The emitter 220 may include a material that emits electrons. In one embodiment, for example, the emitter 220 may include a metal, silicon, an oxide, a diamond, a diamond-like carbon ("DLC"), a carbide compound, a nitrogen compound, a carbon nanotube, a carbon nanofiber, or a combination thereof.

As the area where the emitter 220 occupies in the cathode block 200 is greater, more electrons are emitted by the cathode block 200. However, an electrostatic force generated by a voltage difference between the emitter 220 and the gate electrode 240 may act on the emitter 220. As such, in an embodiment, the gate spacer 230 and the emitter 220 are alternately arranged, and the gate electrode 240 with the opening H is arranged on the area where the emitter 220 is arranged, and thus, a large size cathode block 200 may be provided. In such an embodiment, the gate electrode 240 includes a gate bridge 240b that is arranged in a direction substantially perpendicular to the longitudinal direction of the emitter 220, and thus, a substantially uniform electric field may be formed on the surface of the emitter 220.

In an embodiment, the emitter 220 may be arranged under the gate bridge 240b, and emission of electrons under the gate bridge 240b is minimized. As such, the interval d2 between the gate bridges 240b may be greater than the width w2 of the gate bridge 240b. In such an embodiment, the interval d2 between the gate bridges 240b may be less than twice the distance between the emitter 220 and the gate electrode 240.

X-rays may be generated via an electric field scheme from the above-described structure. In such an embodiment, some of the electrons emitted from the emitter 220 may be incident on the anode block 300, but some of the electrons may collide with the gate electrode 240. The electrons that collide with the gate electrode 240 may be incident on the gate electrode such that a leakage current may occur. As such, as the voltage difference between the cathode electrode 210 and the gate electrode 240 increases, the cathode block 200 may be thermally overloaded. In particular, if heat is generated by the gate electrode 240, the gate electrode 240 may become loose, and thus, an electric short may occur between the gate electrode 240 and the emitter 220. In an embodiment of the x-ray generator, according to the invention, the heat sink 400 may be arranged to contact the cathode block 200 such that heat generated by the gate electrode 240 may be effectively externally dispersed through the gate spacer 230, the cathode electrode 210 and the heat sink 400. As such, loosening of the gate electrode 240 may be effectively prevented.

In an embodiment, the volume of the heat sink 400 is determined based on the emitting area of the emitter 220. In one embodiment, for example, as the volume ratio of the heat sink 400 to the emitting area of the emitter 220 increases, the heat sink efficiency may increase. The heat sink efficiency is large when the volume ratio is in the range of about $10^{-3}$ to about 0.5. In such an embodiment, as the number of the emitters 220 increases, the volume ratio of the heat sink 400 may decrease because electrons may be emitted at a smaller voltage and the overload may less occur as the number of emitters 220 increases.

Hereinafter, current variation and temperature change in a gate electrode of a cathode block in an embodiment of the invention will be described with reference to FIGS. 4A to 5B.

Figure 4A:
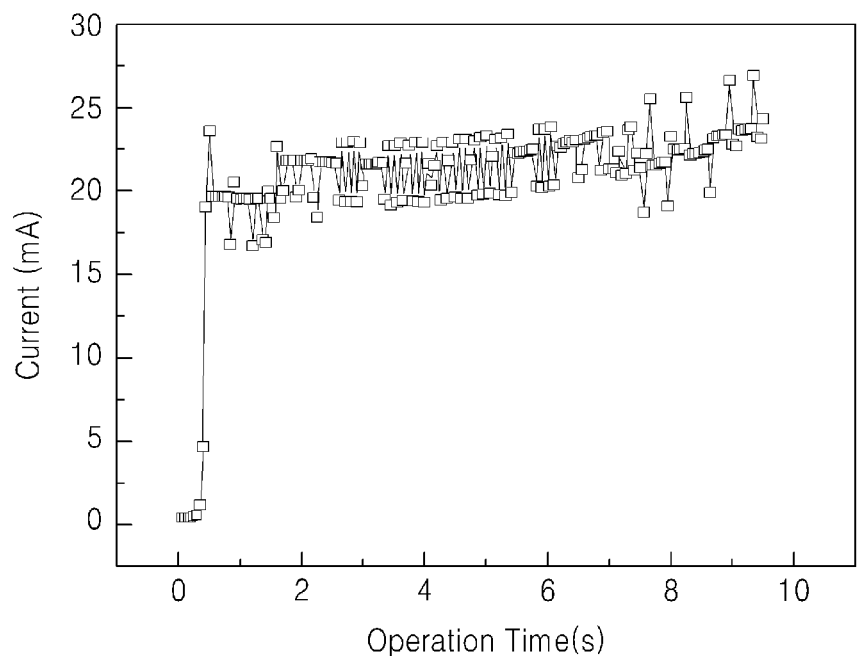
FIG. 4A is a graph illustrating a variation of a current of a gate electrode with time in a state where a heat sink is not used.
Figure 4B:
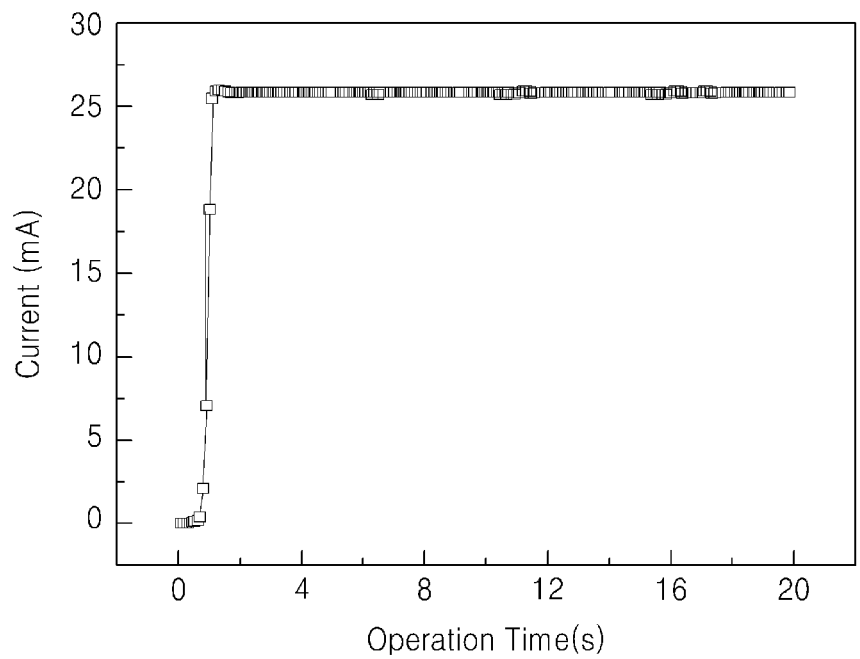
FIG. 4B is a graph illustrating a variation of a current of a gate electrode with time in a state where a heat sink is used.

An exemplary experiment was performed to check the performance of a cathode block according to use of a heat sink. In the experiment, two cathode blocks having the same characteristics were prepared, and the heat sink was arranged on only one cathode block of the two cathode blocks. Regarding the cathode blocks, the gate electrode was made of Invar®, the width of the gate line and the gate bridge was about 25 micrometers (μm), the width of the opening was about 50 μm, and the thickness of the gate electrode was about 30 μm. In the experiment, a voltage was applied between the cathode electrode and the gate electrode in a state where no voltage was applied to the anode electrode. Then, most of the electrons emitted from the emitter were incident on the gate electrode. FIG. 4A is a graph illustrating a current variation of a gate electrode with time in a state where no heat sink was arranged on the cathode block, and FIG. 4B is a graph illustrating a current variation of a gate electrode with time in a state where the heat sink was arranged on the cathode block.

As illustrated in FIG. 4A, when no heat sink was used, an electric current flowing to the gate electrode vibrated, after a certain period of time, for example, about 10 seconds, no current flew to the gate electrode. That is, a short occurred in the cathode electrode that did not include the heat sink. However, when the heat sink was used, a current continuously flew to the gate electrode and no short occurred even after 10 seconds.

Another exemplary experiment was performed to check the heat generation state of a cathode block according to the use of a heat sink, two cathode blocks having the same characteristics were prepared, the above-described heat sink block was arranged on only one cathode block among the two cathode blocks. In the cathode blocks used in the experiment, the gate electrode was made of Invar®, the width of the gate line and the gate bridge was about 25 μm, the width of the opening was about 50 μm, and the thickness of the gate electrode was about 30 μm.

Figure 5A:
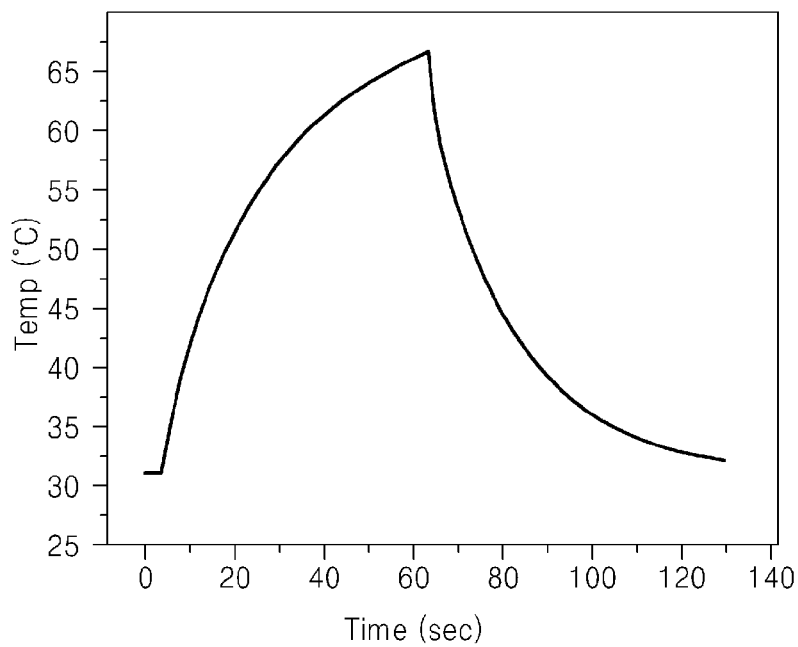
FIG. 5A is a graph illustrating a temperature change of a gate electrode with time in a state where a heat sink is not used.
Figure 5B:
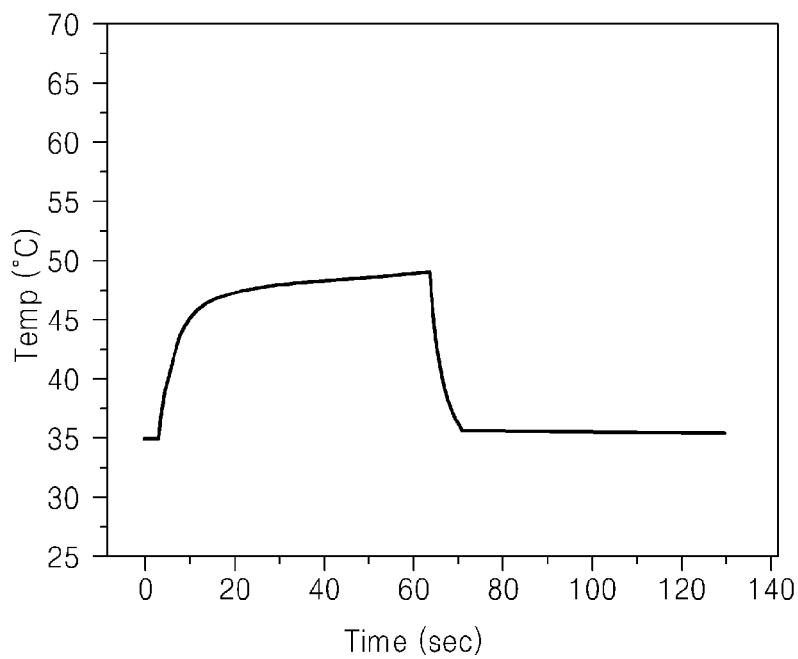
FIG. 5B is a graph illustrating a temperature change of a gate electrode with time in a state where a heat sink is used.

In the experiment, the cathode blocks were controlled so that a current of about 5 milliampere (mA) passed thereto for about 60 seconds. FIG. 5A is a graph illustrating a temperature change of a gate electrode with time in a state where no heat sink is arranged on the cathode block, and FIG. 5B is a graph illustrating a temperature change of a gate electrode with time in a state where the heat sink is arranged on the cathode block.

As illustrated in FIG. 5A, when no heat sink is used, the temperature of the gate electrode continues to rapidly increase while a current is applied to the cathode block. However, when the heat sink is used, the temperature of the gate electrode may gradually increase at a temperature of about 45° C.

Figure 6:
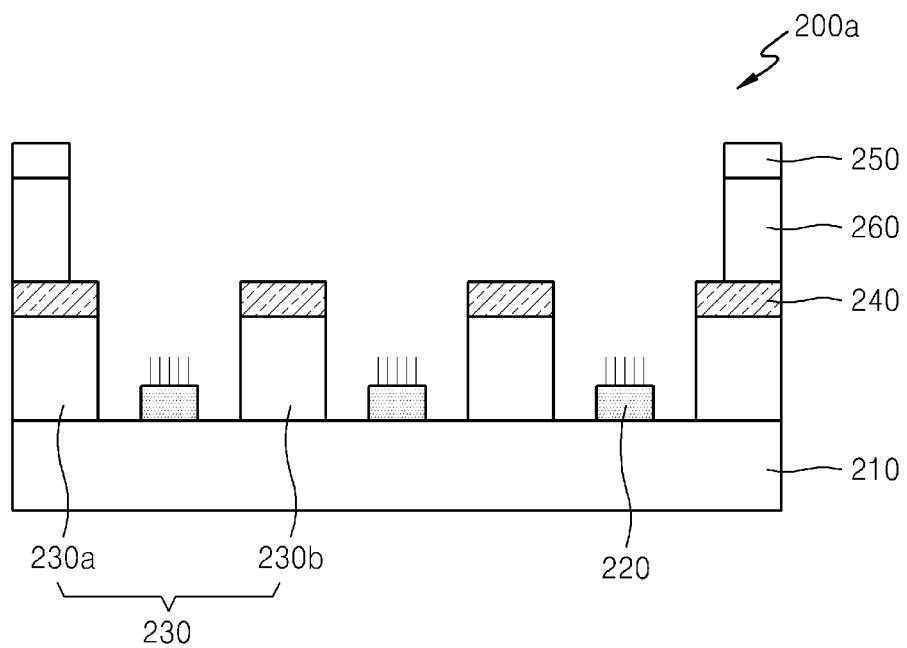
FIG. 6 is a cross-sectional view of an alternative embodiment of a cathode block, according to the invention.

FIG. 6 is a cross-sectional view of an alternative embodiment of a cathode block 200a, according to the invention.

As illustrated in FIG. 6, in an embodiment, the cathode block 200a is arranged separately from the gate electrode 240, and may further include a focusing gate 250 that focuses electrodes and a focusing spacer 260 that is arranged between the gate electrode and the focusing electrode 250 and effectively prevents a short between the gate electrode 240 and the focusing electrode 250. The focusing electrode 250 and the focusing spacer 260 may have a ring shape with an empty hole in the central area. In such an embodiment, the electrons that pass through the central part of the focusing electrode 250 are focused. The voltage applied to the focusing electrode 250 may be substantially equal to the voltage applied to the gate electrode 240, and thus, optimal focusing performance may be maintained.

Figure 7:
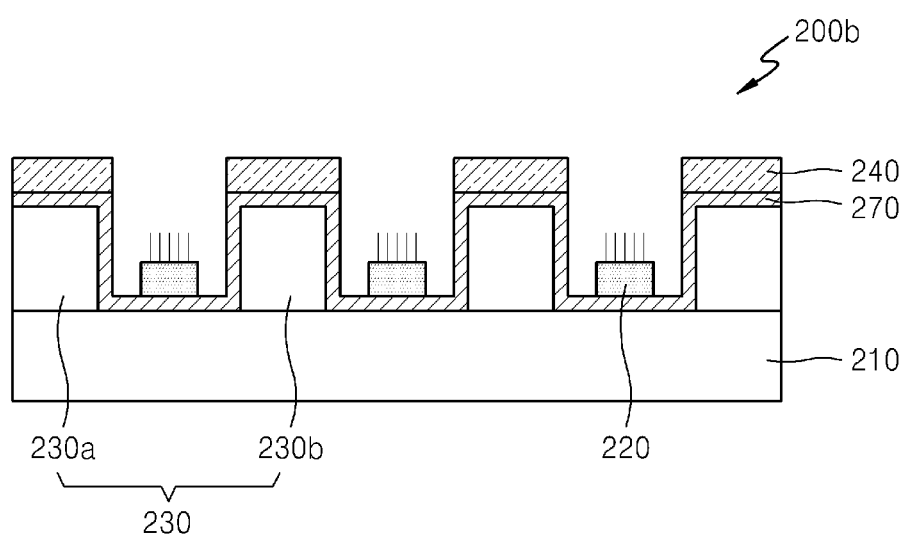
FIG. 7 is a cross-sectional view of another alternative embodiment of a cathode block, according to the invention.

FIG. 7 is a cross-sectional view of another alternative embodiment of a cathode block 200b, according to the invention.

As illustrated in FIG. 7, in an embodiment, the cathode block 200b may further include a charge prevention film 270 that is arranged on the gate spacer 230 and effectively prevents the electrons generated in the emitter 220 from being charged in the gate spacer 230. The charge prevention film 270 may cover the gate spacer 230. The charge prevention film 270 may extend to the cathode electrode 210 between the gate spacers 230. The emitters 220 may be arranged on the gate spacers 230 arranged on the cathode electrode 210. The thickness of the charge prevention film 270 may be less than about 500 angstroms (Å). The charge prevention film 270 may include a material having a resistivity between the resistivity of the gate spacer 230 and the resistivity of the gate electrode 240.

The electrons emitted from the emitter 220 are generally emitted to the outside through the opening H within the cathode electrode 210. However, some of the electrons emitted from the emitter 220 may be incident on the charge prevention film 270. In such an embodiment, where the resistivity of the charge prevention film 270 is less than the resistivity of the gate spacer 230 and is greater than the resistivity of the gate electrode 240, the electrons incident on the charge prevention film 270 move to the gate electrode 240 having a high electrical potential. As such, electric charge of the gate spacer 230 may be effectively prevented and arcing may be substantially reduced. In such an embodiment, the charge prevention film 270 is arranged between the emitter 220 and the gate spacer 230, such that electric charge of the gate spacer 270 may be effectively prevented.

In an embodiment, the charge prevention film 270 may cover the entire gate spacer 230. In an alternative embodiment, the charge prevention film 270 may be arranged only in an area where the collision of the electrons with the gate spacer 230 may be prevented. In one embodiment, for example, the charge prevention film 270 may be arranged only on a sidewall of the gate space 230.

In an embodiment, the charge prevention film 270 or the gate spacer 230 may be arranged with a greater tilt angle compared to the electron emitting source to minimize collision of the electrons emitted from the electron emitting source with the charge prevention film.

Figure 8:
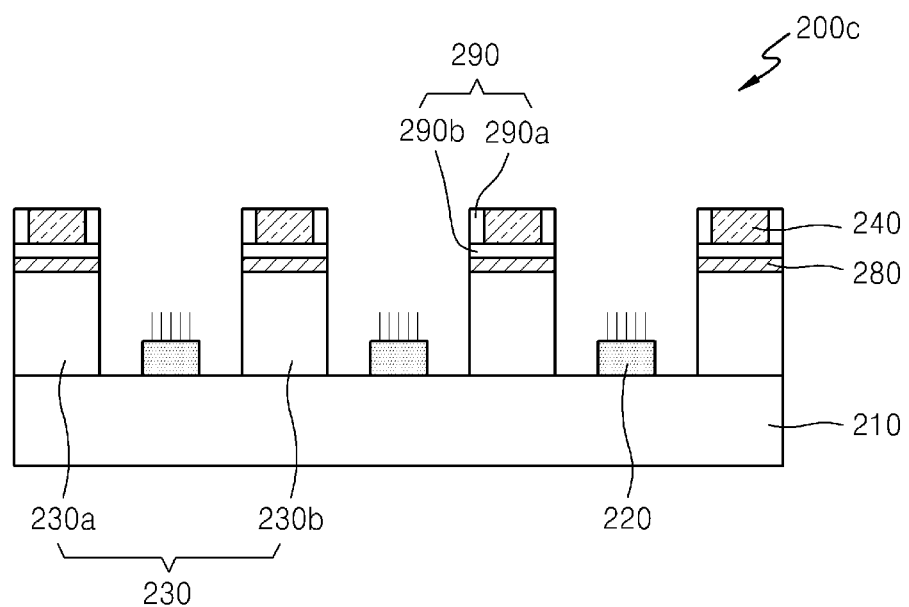
FIG. 8 is a cross-sectional view of another alternative embodiment of a cathode block, according to the invention.

FIG. 8 is a cross-sectional view of another alternative embodiment of a cathode block 200c, according to the invention.

As illustrated in FIG. 8, in an embodiment, the cathode block 200c may further include a bonding layer 280 between the gate electrode 240 and the gate spacer 230 to attach the gate electrode 240 to the gate spacer 230. The bonding layer 280 may include glass. In one embodiment, for example, the bonding layer 280 may include glass frit. The gate electrode 240 may be bonded with the gate spacer 230 via the bonding layer 280 such that separation of the gate electrode 240 from the gate spacer 230 due to the high electric field between the gate electrode 240 and the cathode electrode 210 may be effectively prevented.

In such an embodiment, the cathode block 200c may further include a first secondary electron emitting layer 290a on the sidewall of the gate electrode 240 and may further include a second secondary electron emitting layer 290b on the lower surface of the gate electrode 240. The first secondary electron emitting layer 290a may induce one or more secondary electron emissions from the emitter 220. When the second secondary electron emitting layer 290b is arranged on the lower surface of the gate electrode 240, a surface of the second secondary electron emitting layer 290b may be externally exposed. The primary electrons may be incident on the exposed surface and may be amplified to one or more secondary electrons. Thus, when the second secondary electron emitting layer 290b is additionally arranged on the lower surface of the gate electrode 240, the efficiency of the electron emission, where the primary electrons emitted from the emitter 220 are amplified to the secondary electrons in the secondary electron emitting layer, may increase. In such an embodiment, the first secondary electron emitting layer 290a and the second secondary emitting layer 290b may be integrally formed as a single unitary and indivisible unit. The first and second secondary emitting layers 290a and 290b may include a metal oxide or an inorganic material. In one embodiment, for example, the first and second secondary emitting layers 290a and 290b may include $SiO_2$, $MgO$, $Al_2O_3$, or a combination thereof.

As described above, according to embodiments of the invention set forth herein, the gate electrode has a mesh structure, and thus, a uniform electric field may be formed.

In such embodiments of the invention, a heat sink for externally dispersing heat generated by the cathode block is provided, and thus, deterioration of the cathode block by heat may be effectively prevented.

It should be understood that the exemplary embodiments described therein are to be considered in a descriptive sense only and not for purposes of limitation. Descriptions of features or embodiments within each embodiment should typically be considered as available for other similar features or embodiments in other embodiments.

What is claimed is:

1. An x-ray generator comprising:
    a housing;
    a cathode block which is arranged in the housing and emits electrons via a field emission scheme;
    an anode block which is arranged in the housing and generates x-rays in response to the electrons which are emitted from the cathode block and collide with the anode block; and
    a heat sink which contacts the cathode block and disperses heat generated therein to an outside of the housing,
    wherein the cathode block comprises:
        a cathode electrode;
        a plurality of emitters arranged on the cathode electrode;
        a mesh-type gate electrode spaced apart from the cathode electrode;
        an insulating layer arranged between the cathode electrode and the mesh-type gate electrode and comprising a plurality of gate spacers which are alternately arranged with the emitters; and
        a charge prevention film arranged on the insulating layer, and
    wherein the charge prevention film prevents the insulating layer from being electrically charged by electrons generated by the emitters, and
    wherein a portion of the heat sink is exposed to the outside of the housing.

2. The x-ray generator of claim 1, wherein a concave-convex portion is defined on the exposed portion of the heat sink.

3. The x-ray generator of claim 1, wherein
    the heat sink has a pillar shape,
    one side of the pillar shape contacts the cathode block, and
    another side of the pillar shape is exposed to the outside of the housing.

4. The x-ray generator of claim 1, wherein the heat sink has a shell shape having an empty space defined therein.

5. The x-ray generator of claim 1, wherein the heat sink has a circular cross-section, an oval cross-section, or a polygonal cross-section.

6. The x-ray generator of claim 1, wherein the heat sink comprises at least one of Cu, Al, Cr, Invar, ITO, Mo, and W.

7. The x-ray generator of claim 1, wherein an inside of the housing is in a vacuum state.

8. The x-ray generator of claim 1, wherein a number of the emitters is substantially inversely proportional to a volume of the heat sink.

9. The x-ray generator of claim 1, wherein the cathode block further comprises:
    a bonding layer arranged between the insulating layer and the mesh-type gate electrode.

10. The x-ray generator of claim 9, wherein the bonding layer comprises glass.

11. The x-ray generator of claim 9, wherein the bonding layer comprises glass frit.

12. The x-ray generator of claim 1, wherein each of the emitters comprises carbon nanotubes.

13. The x-ray generator of claim 1, wherein
    a plurality of openings is defined in the mesh-type gate electrode, and
    at least a portion of each of the emitters is exposed by the openings, respectively.

14. The x-ray generator of claim 1, wherein at least one of the insulating layer and the emitters has a line shape.

15. The x-ray generator of claim 1, wherein
    the insulating layer comprises a plurality of gate spacers, and
    the charge prevention film is arranged at a side surface of the gate spacers and is connected to the mesh-type gate electrode.

16. The x-ray generator of claim 1, wherein a resistivity of the charge prevention film is between a resistivity of the mesh-type gate electrode and a resistivity of the gate spacers.

* * * * *